(12) United States Patent
Mehta

(10) Patent No.: US 6,620,439 B1
(45) Date of Patent: Sep. 16, 2003

(54) CHRONO DELIVERY FORMULATIONS AND METHOD OF USE THEREOF

(76) Inventor: Atul M. Mehta, 76 Walsh Dr., Mahwah, NJ (US) 07430

( * ) Notice: Subject to any disclaimer, the term of this patent is extended or adjusted under 35 U.S.C. 154(b) by 0 days.

(21) Appl. No.: 09/678,335

(22) Filed: Oct. 3, 2000

(51) Int. Cl.$^7$ .................................................. A61K 9/16
(52) U.S. Cl. ...................................... 424/497; 424/490
(58) Field of Search .................................. 424/497, 490

(56) References Cited

U.S. PATENT DOCUMENTS

| | | | |
|---|---|---|---|
| 4,721,619 A | 1/1988 | Panoz et al. ................. | 424/459 |
| 4,894,240 A | * 1/1990 | Geoghegan ................. | 424/497 |
| 5,229,135 A | 7/1993 | Philippon et al. ........... | 424/494 |
| 5,286,497 A | * 2/1994 | Hendrickson ............... | 424/490 |
| 5,288,505 A | 2/1994 | Deboeck et al. ............ | 424/497 |
| 5,336,504 A | 8/1994 | Geoghegan et al. ........ | 424/462 |
| 5,788,987 A | 8/1998 | Busetti et al. .............. | 424/480 |
| 5,834,023 A | * 11/1998 | Chen .......................... | 424/497 |

OTHER PUBLICATIONS

Urquhart, J., *Performance Requirements for Controlled–Release Dosage Forms: Therapeutic and Pharmacological Perspectives* (1979), Controlled–Release Pharmaceuticals, American Pharmaceutical Association, pp. 1–48.

Andreotti, et al., *Major Circadian Fluctuations in Fibrinolytic Factors and Possible Relevance to Time of Onset of Myocardial Infarction, Sudden Cardiac Death and Stroke* (1988), The American Journal of Cardiology, vol. 62, pp. 635–637.

Ridker, et al., *Circadian Variation of Acue Myocardial Infarction and the Effect of Low–Dose Aspirin in a Ramdomized Trial of Physicians* (1990), Circulation, vol. 82(3), pp. 897–902.

Braunwald, E., W. B. Saunders Company, *Clinical Features of Acute Myocardial Infarction* (1988), Heart Disease, vol. 2, pp. 1234–1225.

* cited by examiner

Primary Examiner—Michael G. Hartley
Assistant Examiner—Konata M George
(74) Attorney, Agent, or Firm—Kenyon & Kenyon

(57) ABSTRACT

A dosage formulation for once daily administration prior to sleeping is described that provides an initial delay in pharmaceutical release followed by controlled release of the pharmaceutical. There is also provided a method for preparing a time specific delayed, controlled release formulation of dosage, which method includes coating a single pellet with at least one dosage layer, which is coated by at least one seal coat and at least one outer rate controlling layer of a water soluble polymer coat. The dosage formulation of this invention provides substantially a drug free interval of about 0 to 5 hours followed by a drug delivery interval at a rate permitting bioavailability thereof for up to about 24 hours following oral administration. A method of using the formulations of the present invention for the treatment of early morning pathologies is also described.

20 Claims, 3 Drawing Sheets

Drug Chrono Delivery Schematic

1=Rate Controlling membrane
2=Seal Coat
3=Drug Layer
4=Core

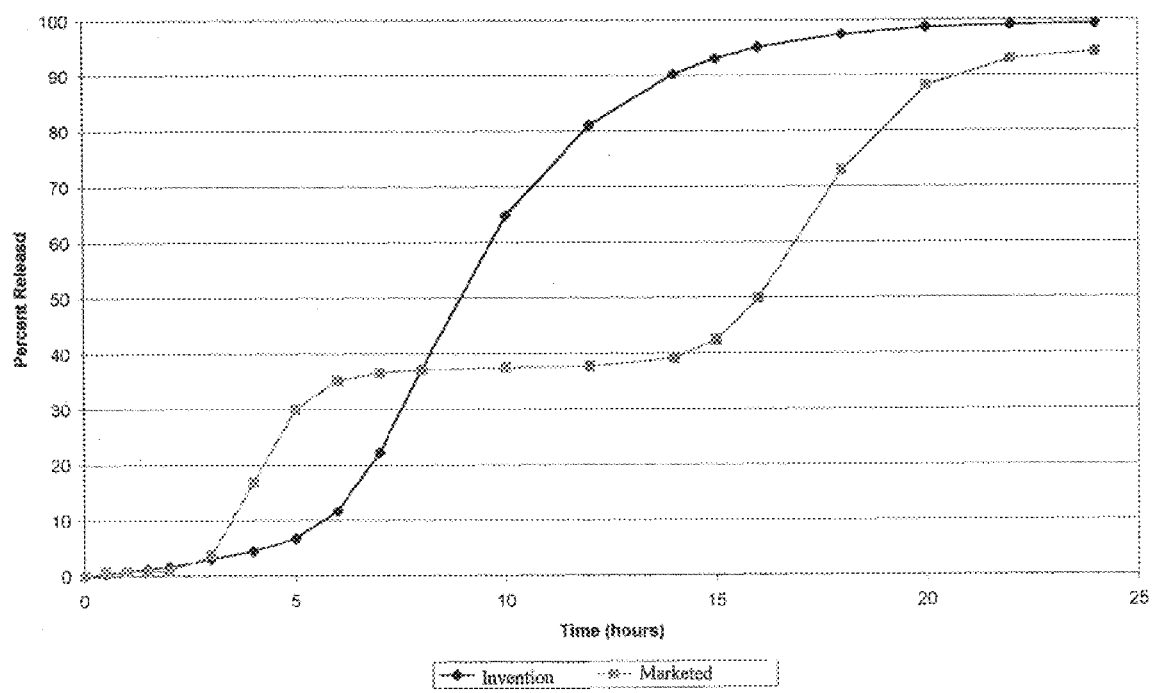

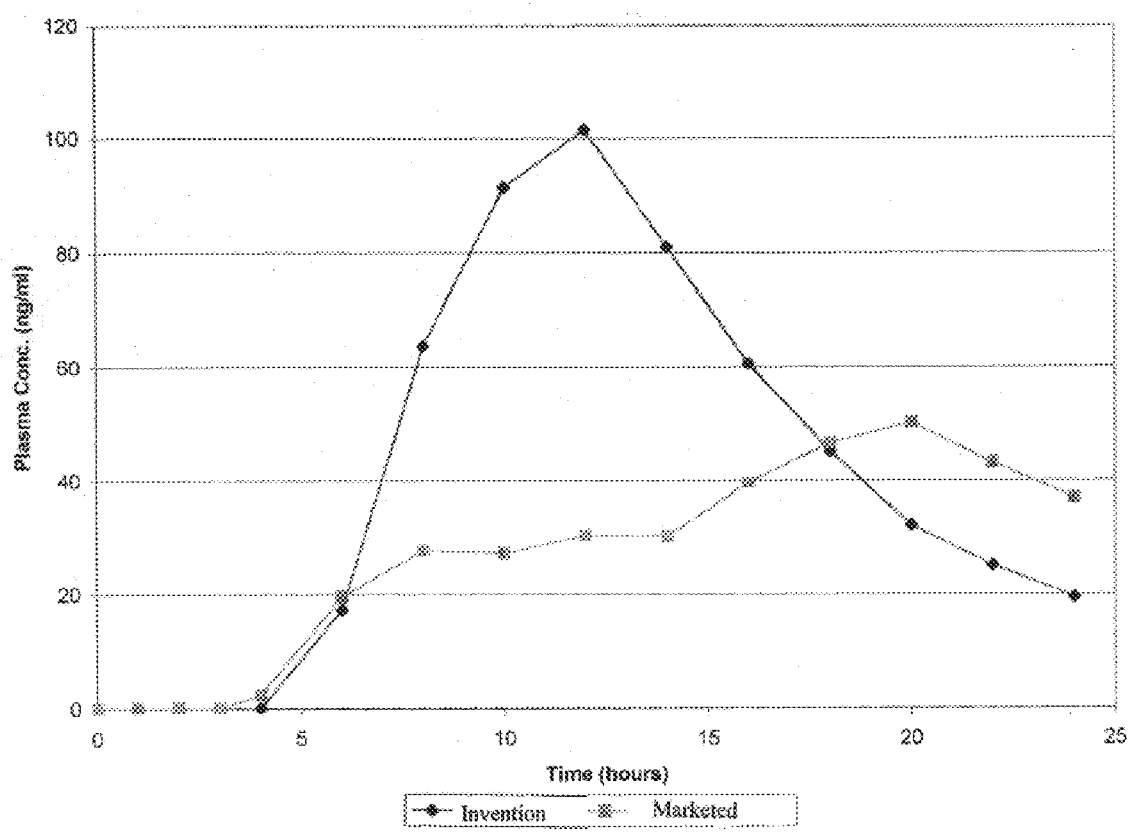

US 6,620,439 B1

CHRONO DELIVERY FORMULATIONS AND METHOD OF USE THEREOF

FIELD OF THE INVENTION

This invention relates to novel oral pharmaceutical formulations of a dose of therapeutic agent for once daily administration prior to sleep having excellent time specific controlled release properties. A substantial percentage of the controlled release dose reaches the blood stream during the dosing period of 5 to 24 hours following oral administration. The method for preparing the formulations provides pharmaceutical preparations for oral administration in both tablet and capsule dosage form.

BACKGROUND OF THE INVENTION

A need exists for a dosage form that makes a drug or therapeutic agent available at a predetermined later time after administration to satisfy a therapeutic demand. The demand can arise during a circadian or chronological cycle of a patient, or there may be a demand for producing a therapeutic effect at a specific later time, such as during the morning hours to treat early morning pathologies. For example, many patients with heart disease exhibit a clinical incidence of infarction that shows a circadian distribution with high frequency in the morning hours between 4:00 a.m. and 9:00 a.m., as reported in The American Journal of Cardiology, Vol. 62, pages 635 to 637, 1988; Circulation, Vol. 82, pages 897 to 902, 1990; and Heart Disease, Vol. 2, pages 1234 to 1235, 1988. Similarly, patients suffering from arrhythmia or angina, as well as other pathologies, such as incontinence, asthma, arthritis or Parkinson's disease exhibit an incidence of clinical symptoms in the early morning hours or upon awakening.

As is well known, the maximum time effectiveness in many pharmaceutical preparations containing a drug is only a few hours because of biological modification and elimination of the medication in the body. Consequently, repeated doses must be taken at frequent intervals to obtain long term therapeutic levels of drugs. After high initial peak concentrations, the level of drug in the blood stream continually decreases due to biological elimination, so there is little or no therapeutic effect at the end of the period between doses. As a result, the therapeutic effect fluctuates between doses corresponding to the peaks and valleys in the level of drug in blood.

Many attempts have been made to develop time-release pharmaceutical preparations which provide a more constant level of the drug in blood over several hours. Successful development of such time-release medications is greatly dependent on the pharmacokinetics of the drug used in such medications. Typically, drugs that are subject to a first pass effect are considered to have non-linear pharmacokinetics and have not been very responsive to time-release manipulations. An increase or decrease in the administered dose of these drugs will not necessarily produce the corresponding increase or decrease in observed blood levels. Thus, it is recognized that it can be difficult to design extended release formulations for compounds subjected to a first pass effect. See for example, Urquhart et al., CONTROLLED-RELEASE PHARMACEUTICALS, American Pharmaceutical Association (1979). Diltiazem is one such drug.

Diltiazem, (+)cis 3-(acetyloxy)-5-[2-(dimethylamino (ethyl]-2,3-dihydro-2-(4-methoxyphenyl)-1,5-benzothiazepin-4 (5H)one, is a calcium antagonist that is utilized in the treatment of cardiovascular disorders such as angina, arrhythmias, and hypertension. Typical doses range from 120–360 mg/day. Diltiazem is sold commercially in extended release pharmaceutical diltiazem forms in order to maintain a therapeutic serum level of diltiazem and to minimize the effects of missed doses of drugs caused by a lack of patient compliance. The minimum therapeutic plasma diltiazem concentrations are in the range of about 50 to 200 ng/ml.

The activity of diltiazem in humans is directly related to its blood or plasma concentration. For illnesses which require continuous and constant control, such as hypertension and angina pectoris, diltiazem must be administered every 6 to 8 hours, as it has a very short half-life in blood of only about 3 to 4 hours. After each administration of diltiazem a succession of rapidly increasing and decreasing plasmatic diltiazem concentrations is established. Thus, the patient being treated and the target organ, more particularly the heart, are alternatively subjected to overdoses and underdoses of medicine.

The pharmacokinetics of diltiazem have been studied extensively. Diltiazem is well absorbed from the gastrointestinal tract and is subjected to an extensive first pass effect giving an absolute bioavailability of 40% (when compared with intravenous administration.) At therapeutic doses, approximately 60% of the administered diltiazem is metabolized before the compound has had a chance to reach its site of action, resulting in sub-therapeutic levels of the drug over a significant portion of the dosing period. Accordingly, it is important that the level of diltiazem maintained in blood plasma of a patient be relatively constant within the effective diltiazem range for the entire diltiazem.

In order to alleviate these drawbacks, a first form of sustained-released diltiazem known under the trade name, CARDIZEM SR.RTM., was developed and presented in the form of "erodible pellets", for once a day administration (Geoghegan et al.: U.S. Pat. Nos. 4,721,619; 4,894,240; and 5,336,504). These patents disclose a diltiazem formulation suitable for once a day administration. The formulation is prepared from diltiazem beads in which a diltiazem core is enveloped by a multilayer film having as a major component a water insoluble polymer and a minor component of a water soluble polymer. The number of layers used in the building up process, as described in the above-noted patents, is between 50 and 200 layers for the core and between 20 and 40 layers of polymer coating for the membrane.

The number of layers in the membrane and the ratio of water soluble to water insoluble polymer affects the rate of release of diltiazem from pellets. Geoghegan et al. specify that from 60% to 95% of the diltiazem should be released from the controlled release diltiazem form within 13 hours of administration. This release pattern produces peak plasma levels approximately 12–14 hours after administration.

The problem with this formulation is that optimum blood levels of diltiazem over the entire 24 hour dosing period are not maintained. Blood levels of diltiazem fall significantly before the next dose is administered resulting in a significant variance between peak and valley levels. Accordingly, although this formulation affords a reduction in peak concentration and in the number of daily intakes from 4 to 2, it does not eliminate high diltiazem blood concentration between successive medication intakes. Hence, the patient is still obliged to take the medication twice daily. Moreover, the solvent of the polymer solution used to make the membrane is constituted by organic solvents, such as isopropanol, methanol, acetone, and methylene chloride which are dangerous to use due to their flammability and toxicity, thus undesirable for an oral formulation.

U.S. Pat. No. 4,721,619 to Panoz et al. discloses a controlled absorption diltiazem formulation having a pellet of diltiazem in association with an organic acid and a lubricant, coated with a pH independent polymer. The release of 100% of diltiazem is achieved after 12 hours in vitro.

An extended-release form of diltiazem is disclosed in U.S. Pat. No. 5,288,505 to Deboeck et al. This formulation contains diltiazem as an active ingredient and a wetting agent, being coated with a microporous membrane, which membrane includes at least a water-soluble or water-dispersible polymer or copolymer and a pharmaceutically acceptable adjuvant. This formulation provides a single layer of a drug coated with several layers of membranes.

A sustained release formulation for oral administration is disclosed in U.S. Pat. No. 5,229,135 to Philippon et al. This formulation provides a pellet having a central sugar sphere and a plurality of alternating first and second layers surrounding the sphere to form a core, the first layer is a water soluble polymeric material, the second layer is diltiazem, and the outer layer is a water insoluble polymeric material. This formulation provides a single drug layer being sandwiched between water soluble and water insoluble polymers.

U.S. Pat. No. 5,286,497 to Hendrickson discloses a diltiazem formulation for Cardizem.RTM.CD, which has a "stair-step release profile" containing rapid release beads and extended release beads. This formulation is marketed as a once a day extended release capsule containing diltiazem and fumaric acid and provides for a blend of diltiazem beads having two dissolution profiles; rapid release profile and delayed release profile. Each of the rapid release and delayed release diltiazem beads is comprised of two parts. The first part is a central core which contains the diltiazem in association with conventional excipients (diltiazem blend), and the second part is a polymeric coating, which is a different polymer in rapid release beads, as opposed to delayed release beads.

U.S. Pat. No. 5,834,023 to Chen describes a once a day controlled release diltiazem formulation which includes enteric polymeric membrane coated pellets comprising a biologically inert core which is coated with a first layer that consists of diltiazem and a polymeric binder; and a second layer that consists of a pH dependent polymeric material. The formulation additionally has a delayed pulse polymeric membrane coated pellet which contains a biologically inert core coated with diltiazem and a polymeric binder and a second polymeric membrane which is pH independent. This formulation provides a multiple cores of the biologically inert pellet in one tablet.

U.S. Pat. No. 5,788,987 to Busetti et al. discloses a therapeutic dose formulation that provides an initial delay in release of the therapeutic agent therefrom, followed by controlled release of the therapeutic agent. Release of the therapeutic agent is controlled by use of a core including the therapeutic agent, which is coated with a swellable polymeric coating. The release rate is controlled by adjusting the thickness of the coating.

It is immediately apparent in the light of the above that a pressing need exists for a dosage form that can delay the delivery of a drug, such as diltiazem to provide a drug-free interval and then deliver an effective dose of therapeutic agent specifically at a time when needed most and for a sustained period. The present invention provides such formulations.

SUMMARY OF THE INVENTION

In a first aspect of the invention there is provided a formulation for administration of a therapeutic agent for treatment of pathologies typically occurring in the morning hours, or upon awakening. The formulation of the present invention is administered once daily prior to sleep and comprises a biologically inert pellet comprising:

a drug layer comprising a dosage form of a pharmaceutical agent and a binder agent, said binder agent and said pharmaceutical agent being present in a ratio of about 0.5:20; and a rate controlling layer comprising a water insoluble polymer, said water insoluble polymer being present in a total amount in the range of from about 5–12% of the total weight of the dosage formulation, wherein release of the drug from the dosage formulation comprises a substantially delayed release followed by sustained release of the drug. In a preferred embodiment, the drug layer is coated with a sealing layer.

In another aspect of the invention there is provided a method of treating, preventing, or controlling hypertension or angina, in a subject in need thereof, which comprises administering to a patient in need of such treatment the dosage formulation of the invention as defined above once daily prior to sleeping.

BRIEF DESCRIPTION OF THE DRAWINGS

FIG. 2 is a graph of the in vitro release of diltiazem from the present chrono delivery formulation and the currently marketed Cardizem CD over a twenty-four hour period.

FIG. 3 is a graph of the in vivo plasma concentration of diltiazem at various times post administration of the chrono release diltiazem formulation of the invention and the currently marketed Cardizem CD over a twenty-four hour period.

DETAILED DESCRIPTION OF THE INVENTION

Figure 1:
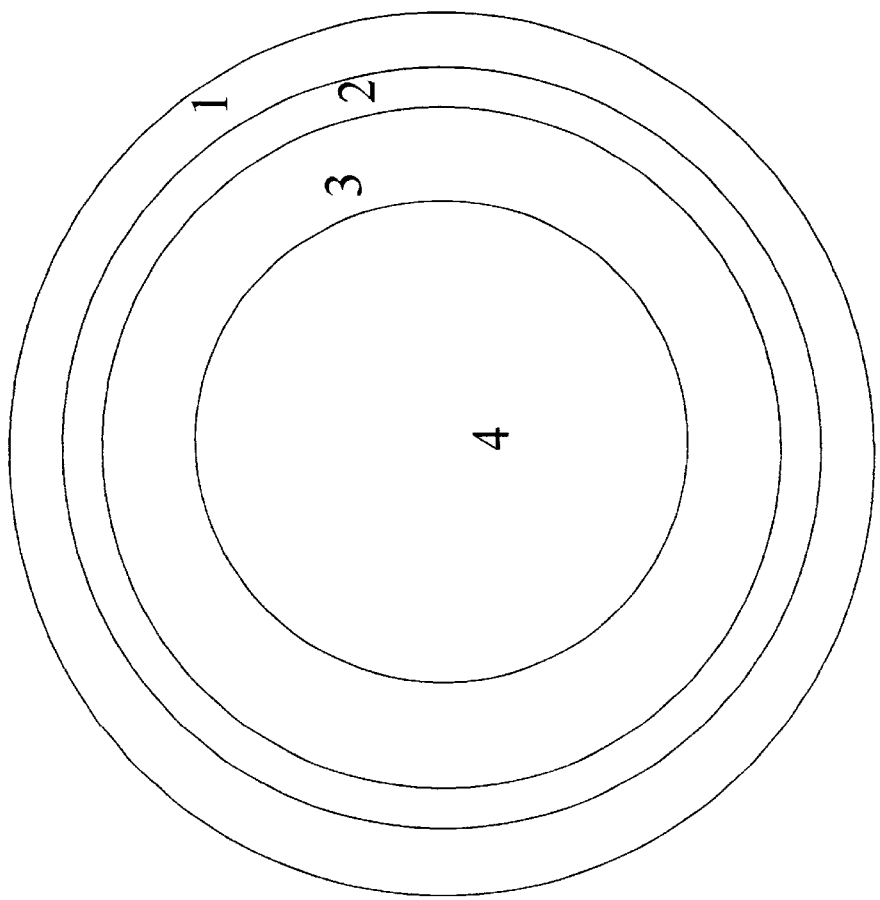
FIG. 1 is a schematic of the core of the structure of a diltiazem chrono delivery formulation.

This invention, as disclosed and described herein, provides for a novel time specific delayed release dosage formulation of a therapeutic agent, such as diltiazem, for administration prior to sleeping to treat pathologies that typically occur in the morning hours or upon awakening. This invention provides a dosage formulation that optimizes drug levels at the early morning hours of the dosing period by providing a formulation which exhibits a substantially drug free interval, followed by a drug delivery interval of a period of about 5 to 20 hours following oral administration. Additionally, the dosage formulation, as described herein, provides for a single pellet formulation which requires no mixing and, therefore, permits easy and more accurate manufacturing of the formulation. The dosage formulation of the present invention is referred to herein as a "chrono release" formulation due to its initial time specific delayed release of drug diltiazem, followed by sustained release of drug for up to about 5 to 20 hours following the delayed release, and peaking at about 10 to 12 hours after administration.

The present invention provides a dosage formulation and methods for treating morning pathologies, which include pathologies, diseases, disorders, conditions and clinical symptoms that are typically aggravated or often acute during the last hours of sleeping or upon or shortly after awakening. Most humans sleep for a period of from about 3 to about 8 hours during the night and the pathologies are typically exhibited in the morning. However, some people have altered sleep patterns, sleeping during the day and remaining active during the night. Individuals with such altered sleep patterns may exhibit symptoms or pathologies at night or upon awakening. Therefore, for such people with altered sleep patterns, the methods and formulations of this invention may be administered prior to sleeping, irrespective of actual time of day.

Examples of morning pathologies that may be treated by the formulations and methods of the invention include for example angina, hypertension, arrhythmia, infarction, incontinence, arthritis, Parkinson's disease, and asthma. With each of these disorders, symptoms are usually aggravated or worse during the late night-early morning hours, usually when the person is sleeping or just after the person awakens. The term "sleeping" as used herein means a prolonged period of rest or inactivity or decreased activity. The term "sleep" is used to mean those hours of resting when all clinical stages of sleeping are attained as well as those periods of rest when not all of the clinical stages of sleep are not attained. The term "awaken" refers to the period of arousal from sleeping, which is characterized by an increase in activity. The period of awakening includes the time from arousal from sleep to about four hours thereafter.

The dosage formulations and methods of the present invention are useful for treating the foregoing morning pathologies because the present dosage formulations and methods provide therapeutically effective amounts of drug in a time specific controlled release manner, delivering drug to the blood stream at the time needed most. The once daily, prior to sleep administration of the dosage formulation of the invention provides an alternative to prior art dosage formulations, which require the presence of several core pellets, enteric coating polymers, organic acids and solvents, and extensive mixing of pellets to achieve a once a day effect, and/or do not achieve a sustained and optimal amount of drug at a time when needed most, i.e., in the morning hours or upon awakening.

The present invention provides a novel dosage formulation characterized by having a substantially delayed release followed by controlled and sustained release of the active substance. Substantially delayed release followed by sustained release, as the phrase is defined herein, means maintaining the plasma concentration of drug from about 0 to less than about 20 ng from the time of administration to about 5 hours after administration (a substantially drug free interval), followed by an increase of plasma concentration of drug to a peak concentration of drug at about 8 to about 12 hours after administration of the dosage form. The dosage formulations of this invention afford excellent bioavailability while avoiding fluctuating plasmatic concentration peaks, so that it is now possible to maintain drug plasmatic concentrations in a desired, effective range in a circadian fashion while simplifying the administration of the drug to only once daily.

FIG. 3 demonstrates the bioavailability of diltiazem in plasma over a 24 hour period following the administration of a 180 mg diltiazem dosage formulation of the invention. After a 4–5 hour delay following administration, the plasma concentration of the drug substantially and continually increases for about 8–9 hours (peaking at about 10–12 hours after administration of the dosage formulation) and remains at a therapeutically effective level for up to about 20–24 hours following administration. In the case of the diltiazem formulation of the invention containing a dosage of 180 mg diltiazem, the plasma concentration of drug in the blood remains at less than about 20 ng/ml for up to about 5 hours after administration and then increases to a peak concentration of from about 90 to about 120 ng/ml in a sustained and controlled manner.

According to the present invention, the time specific delayed release dosage formulation is characterized by having a biologically inert pellet coated by at least one layer of drug(s) in admixture with a suitable binder agent; which is coated with an outer layer referred to herein as "the rate controlling layer."

In one embodiment of the invention, the drug contained in the drug layer of the pellets is useful for treating myocardial or cerebral infarction. In this embodiment, the pellets may contain a coating of a therapeutically effective amount of diltiazem or a pharmaceutically acceptable salt thereof, or any other drug alone or in combination with diltiazem that is useful in treating infarctions. For example, the pellets may contain an anticoagulant or antiplatelet agent, such as for example, warfarin, acetylsalicylic acid, ticlopidine and the like, alone or in combination with diltiazem. In the case of diltiazem, the pharmaceutically acceptable salts may include the hydrochloride, sulfate or phosphate salts. However, they may also include the acetate, citrate or lactate salts, for example. It is preferred however, that the hydrochloride salt of diltiazem be used.

For treatment of angina, the pellets may contain a coating of a therapeutically effective amount of an antiangina agent such as isosorbide dinitrate or isosorbate mononitrate. For treatment of hypertension or arrhythmia the pellets may contain, alone or in combination, a therapeutically effective amount of calcium antagonists, angiotensin-converting enzyme inhibitors, beta-blockers, any of alpha-antagonists, and the like.

For the treatment of other pathologies, such as incontinence, the pellets may contain a therapeutically effective amount of an anticholinergic or antispasmodic agent or a vasopressin analogue for example. For the treatment of arthritis, the pellets may contain a therapeutically effective amount of an antiarthritis agent such as non-steroidal anti-inflammatory agents, such as diclofenac, ketoprofen, ibuprofen, mesalamine, sulfides, and the like, as well as their pharmaceutically acceptable salts.

The drug layer is applied to biologically inert pharmaceutically acceptable pellets in admixture with a suitable binder agent. Many types of pellets that are suitable for use in the methods and formulations of the present invention are commercially available from a number of pharmaceutical supply companies; for example, non-pareils, sugar and/or starch-based pellets. Non-pareil pellets of particle size 25 to 30 mesh are particularly preferred, although any non-pareil pellet of mesh size within the range of 14 mesh to 60 mesh are also preferred for use in this invention.

Suitable binder agents for use in the drug layer of the coated pellets of the present invention include, for example, water soluble polymers such as hydroxypropylmethyl cellulose (3 to 6 cps, preferably 6 cps), hydroxyethyl cellulose, hydroxypropyl cellulose, methyl cellulose, polyvinylpyrrolidone and the like. Preferably, hydroxypropylmethyl cellulose, and most preferably, hydroxypropylmethyl cellulose-E-6 is used in the practice of the present invention. Preferably the amount of binder agent included in the drug layer is in a ratio of binder agent to drug of from about 0.5:20, preferably about 0.7:10, most preferably about 1:8. The drug layer may also contain a suitable carrier or diluent, and may optionally contain a surfactant.

In a preferred embodiment, the drug layer is coated with an optional sealing layer. The sealing layer contains a water soluble polymer, which may be the same or different from the binder agent present in the drug layer. For example, the sealing agent may include a water soluble polymer such as hydroxypropylmethyl cellulose (3 to 6 cps, preferably 6 cps), hydroxyethyl cellulose, hydroxypropyl cellulose, methyl cellulose, polyvinylpyrrolidone and the like. Preferably, hydroxypropylmethyl cellulose, and most preferably, hydroxypropylmethyl cellulose-E-6 is used in the sealing layer.

The total amount of optional sealing layer contained in the pharmaceutical loaded pellets may be varied depending on the desired release rate of the pharmaceutical agent, e.g., diltiazem-HCl. When the pharmaceutical agent of the pellets is diltiazem, it is preferred that the polymer coating comprise about 0.5% to about 5% of the total weight of the pellet, and most preferably, about 1% to about 2% of the total weight of the pellet.

The outer rate controlling layer contains a water insoluble polymer, which may be ethyl cellulose, a copolymer of acrylic and methylacrylic acid esters, which is physiologically acceptable, water insoluble, and permeable to the release of drug contained in the drug layer. Suitable water insoluble polymers include for example, Eudragit RL 30 D, Eudragit RS 30D, or a poly(meth)acrylate polymer, such as Eudragit NE 30 D, and Eudragit NE 40 D, or a combination thereof. Most preferably, the poly(meth)acrylate polymer, Eudragit NE 30 D, is used in formulating the controlled release coating. Eudragit NE 30 D, Eudragit RS 30 D and Eudragit RL 30 D polymers are available from Rhom Pharma, D-6108 Weiterstadt 1, Dr. Otto-Rohm-Str. 2-4, Germany. Eudragit NE 30 D and Eudragit NE 40 D are pH independent polymers available as a 30% or 40% aqueous dispersion. Eudragit RS 30 D and Eudragit RL 30 D are available as aqueous dispersions containing 30% dry substances.

In a preferred embodiment of the invention the binder agent in the drug layer and the innermost drug sealing layer is hydroxypropylmethyl cellulose and the outer rate controlling layer is Eudragit NE 30 D.

The outer rate controlling layer is prepared as a dispersion and may be mixed with a suspension of lubricant agent, such as calcium stearate, magnesium stearate, zinc stearate, stearic acid, talc or a combination thereof to form the time specific controlled release coating mixture. In particular, it is preferred that the outer rate controlling layer contains an amount of magnesium stearate sufficient to provide delayed release of diltiazem for up to about 4–5 hours after administration. In a most preferred embodiment the outer rate controlling layer contains a combination of magnesium stearate admixed with Eudragit NE30 and may contain simethicone. The final, dried controlled release coating contains about 2% to 10% magnesium stearate or other lubricant, and more preferably about 2.5% to 5.5%, and most preferably about 2.5% to 3.0% magnesium stearate or other lubricant based on the total weight of solids content of the controlled release formulation. The lubricant functions to prevent agglomeration of the coated pellets during processing and also helps to delay release of the pharmaceutical agent from the coated pellets. The presence of an amount of about 2.5% to 3.0% w/w magnesium stearate or other lubricant in the controlled release coating affects the delayed release of the drug for about 4–5 hours following oral administration of the formulation.

In another embodiment of the invention the outer rate controlling layer is coated with an enteric coating polymer, which may also contain a plasticizer. A preferred enteric coating polymer is Eudragit L 30D. Suitable plasticizers for inclusion in the enteric layer include, for example, triethyl citrate, polyethylene glycol, dibutyl phthalate, diethylphthalate and triacetin. The optional enteric coating, which is pH dependant and resistant to gastric fluids may comprise from about 4 to 10%, preferably about 4 to 6% of the total weight of the diltiazem formulation. The enteric coating may also be coated with one or more layers of a sealant or a binding agent.

The drug layer, optional sealing layer, outer rate controlling layer, and optional enteric coating may each further comprise diluents, carriers, fillers and other pharmaceutical additives which may affect the rate of release of active agent(s) from the pellet. For example, the outer rate controlling layer preferably contains a lubricant agent and preferably, the drug layer contains a surfactant. The pellet layers may further contain pharmaceutically acceptable excipients such as anti-adherents, pharmaceutically acceptable pigment such as, titanium dioxide, iron oxide and various color pigments including vegetable dyes, and the like. Preferably, the pharmaceutical loaded pellets of the invention provide in total a potency of approximately 50% (w/w) based upon the total weight of the layered pellets, although the potency can be adjusted as desired. When the pharmaceutical agent included in the layering is diltiazem, it is preferred that the pellet be formulated at about 45 to about 55% potency (w/w) However, the skilled practitioner can make the present dosage formulation at any desired drug potency.

The time specific delayed release formulation, as disclosed herein, permits the release of the drug in a manner to provide and maintain a therapeutic amount of diltiazem in circulation for about 15–24 hours after administration of the formulation, following an approximately 4–5 hour initial delay in drug release. In particular, the delayed release followed by sustained release formulation described herein, when administered prior to sleeping provides optimal concentration of drug when most needed, i.e., in the morning hours or upon awakening.

The process for making the pharmaceutical formulations of the present invention includes coating at least one layer of drug(s) and suitable binder agent onto the surface of a biologically inert pellet; i.e., layered or a non-pareil pellet (sugar and/or starch-based pellets) to form drug loaded pellets. The drug loaded pellets are then optionally enveloped by a sealing layer. The drug loaded pellets (with or without a sealing layer) are finally coated with an outer rate controlling layer. Optionally, the outer controlled release layer may be coated with a sealing layer and/or enteric coating layer.

In preparing the formulations of the invention, the drug layer may be applied by spraying the drug/binder agent solution onto non-pareil or other pellets that have been suspended in a fluidized bed, for example. Other conventional techniques such as pan coating or extruder/marumerizer can also be used. After the pellets are coated with the drug layer they may optionally be dried by air exposure, or other methods known in the art (although drying may occur spontaneously from air flow in the fluid bed processor). Pellets obtained from the drug layering are then optionally fluidized and sprayed with the water soluble, water permeable, and pharmaceutically acceptable polymer coating to form the innermost sealing layer.

Preferably, the sealing agent is dissolved in water to form a 5% to 30% (w/w) solution, preferably a 7% to 25% (w/w) solution and most preferably, an approximately 10% (w/w) solution. The solution of sealing agent is then sprayed onto the pellet using, for example, a fluid processor. The ratio of sealing agent to total weight of the dosage formulation is about 0.5% to about 5%, more preferably from 1% to about 3% (w/w), and most preferably about 2%.

The rate controlling polymer is layered onto the drug loaded and optionally sealed pellets. The polymer comprising the outer rate controlling layer is generally prepared as a dispersion and sprayed onto the prepared pellets. The total amount of rate controlling polymer in the pellets is in the range of from about 5–12% of the total weight of the prepared pellets, preferably about 7–9% of the total weight of the prepared pellets. By varying the amount of rate controlling polymer within this range, a desired predetermined delay followed by sustained release of the therapeutic agent is achieved.

At the final stage the pellets may be subjected to a curing process. The pellets are cured at a temperature in the range of from about 30° to about 50° C., preferably, from about 35° to about 45° C., and most preferably, about 40° C. for a period of about 5 to about 10 days and, preferably, about 7 days. Surprisingly, although others in the art have found shorter curing times to be preferred, the inventor of this invention has found that these long curing times help to stabilize the release of pharmaceutical agent from the pellets even after long storage periods.

The cured coated pellets may be weighed out according to the total dose of pharmaceutical agent to be administered to patients. Diluent may be added, such as, for example, dextrose, sorbitol, mannitol, microcrystalline cellulose, methocel ether, lactose, glyceryl palmitostearate, glyceryl stearate, glyceryl behenate, and combinations thereof, among other commonly used pharmaceutical diluents, and the mixture of coated pellets and diluents pressed into tablets. Alternatively, the mixture of the coated pellets alone or with talc can be encapsulated in a capsule, such as a hard gelatin capsule.

It is often desirable to add inert diluent when formulating the coated pellets into tablet form. The presence of pharmaceutical diluents, such as microcrystalline cellulose, methocel ether, glyceryl palmitostearate, glyceryl stearate, and/or glyceryl behemate, for example, in the pellet mixture serves to cushion the pellets so that they are not significantly ruptured during compression.

In general, the release rate of pharmaceutical agent from the pellets is dependent upon a number of factors including, inter alia, the overall structure and design of the layered pellet, the potency of the layered pellet, the type and amount of polymer present in each of the drug layer, optional sealing layer and outermost layer. The pellets may be formulated into tablets or encapsulated in the desired dosage amount. Typical unit dosage amounts for a once before sleep delayed release tablet for oral administration include any dosage between about 25 and 1000 mg, such as 50, 100, 200, 300, 500, 750 mg.

The dosage formulations of the invention are formulated to provide a sustained release of drug following a predetermined delay in drug release. Preferably, the dosage formulations of the invention provide a release of drug when measured in an aqueous solution in a paddle apparatus according to U.S. Pharmacopeia XXII, that corresponds to the following dissolution profile:

1) from 0 to about 8% release of total drug from 0 to about 5 hours (a substantially drug-free interval);

2) from about 8% to about 90% release of total drug from about 5 to about 15 hours; and 3) release of substantially all of the remaining drug (about 90% to about 100%) from the pellets during the period from 15 hours to 24 hours. It is not necessary that all of the remaining diltiazem is released from the formulation.

The release profile of diltiazem from the formulations of the present invention ensures that after once daily (prior to sleeping) administration of the present dosage formulation a therapeutically effective amount of drug is available in the patient's plasma in the morning hours or upon awakening to treat morning pathologies, such as myocardial infarction.

The following examples are illustrative of the invention, and are not to be construed as limiting the invention.

EXAMPLE 1

Preparation of Diltiazem Formulation

Step I. Inner Drug Layering

| Formulation of Drug Layer | |
|---|---|
| Non-Pareils 25/30 mesh | 800 g |
| Diltiazem hydrochloride (HCl) | 985 g |
| Hydroxypropylmethyl celluiose (HPMC) as 10% w/w solution in water | 1230 g |
| Deionized (DI) water | 740 g |

Method
1. Prepared 10% HPMC solution by dispersing 123 g of HPMC E-6 (6 cps grade of Dow Chemicals) into 1107 g of de-ionized water and mix until clear solution was obtained.
2. Dispersed 985 g diltiazem HCl in 740 ml deionized water and mixed.
3. Added diltiazem solution to HPMC 10% solution and mixed until clear solution was obtained.
4. The solution was then sprayed onto non-pareil pellets using a fluid bed processor.

Step II. Seal Coat Layered Onto Drug Coated Pellets

| Formulation of Innermost Sealing Layer | |
|---|---|
| Diltiazem pellets of Step I | 1882 g |
| HPMC E-6 10% solution in DI water | 376 g |
| DI water | 376 g |

Method
1. Prepared 10% HPMC solution by dispersing 37.6 g of HPMC E-6 (6 cps grade of Dow Chemicals) into 338.4 g of deionized water and mixed until clear solution was obtained.
2. The HPMC solution was sprayed onto diltiazem coated pellets using a fluid bed processor.

Step III. Outer Layering

| Formulation of Outer Rate Controlling Layer | |
|---|---|
| Seal coated layered pellets of Step II | 900 g |
| Eudragit NE30D dispersion | 500 g |
| Magnesium Stearate 15% w/w dispersion | 300 g |

Method
1. Prepared 15% magnesium stearate dispersion by adding 45 g of magnesium stearate to 1.5 g of simethicone emulsion to 255 g of deionized water and mixed until a homogeneous dispersion was made.
2. The Eudragit NE30D dispersion was added to the 15% magnesium stearate/simethicone dispersion and mixed for 15 minutes.

3. 480 g of dispersion was then sprayed onto the drug coated and sealed non-pareils using a fluid bed processor.
4. The pellets were then cured at 40° C. for seven days.

TABLE 1

Diltilite Chrono Formulation Examples

| Ingredients | Example 1 % |
|---|---|
| Non-pareil pellets | 35.7 |
| Diltiazem HC1 | 45.37 |
| HPMC E-6 | |
| Drug Layer | 5.67 |
| Sealing Layer | 1.74 |
| Eudragit NE 30 D solids | 8.85 |
| Magnesium Stearate | 2.65 |
| TOTAL | 100 |

Step IV. Preparation of Capsules

Size #0 capsules were filled with the coated pellets of Step III which were blended with talc (1% w/w). The capsules maybe manually filled or machine filled. The fill weight was adjusted to provide the desired strength (i.e. amount of diltiazem per capsule). For example, 415 mg of pellets of Step III were filled at 43.7% potency to give 180 mg of diltiazem HCl per capsule.

EXAMPLE 2

In Vitro Release of Diltiazem

Dissolution testing of the capsules prepared in Example 1 was performed using USP Method II, 900 ml of water and 100 rpm. The same test and conditions were also used to determine the dissolution rate of diltiazem from the currently marketed Cardizem CD, which contains a dosage of 180 mg diltiazem. The results are shown in FIG. 2.

EXAMPLE 3

In Vivo Delivery of Diltiazem

In a two way cross-over study, eight healthy volunteers were given either a diltiazem capsule as prepared in Example 1 or a capsule of the marketed product, Cardizem CD (180 mg), at 10 P.M. Blood was drawn at various times during the night and the concentration of each of the drugs in the plasma was determined and is shown in FIG. 3. As can be seen, between the hours of 4 and 8 A.M. the plasma concentration of diltiazem increases steadily and is highest at about 12 hours in those patients given the diltiazem formulation of the present invention.

EXAMPLE 4

Treatment of Angina and Hypertension

Pellets are prepared as described in Example 1, compressed into tablet form or capsule form, and formulated to contain a desired dosage of diltiazem, for example, 180 mg formulation. These tablets or capsules are then orally administered to a patient in need of prevention or suffering from angina, hypertension, or other disorder for which diltiazem is indicated prior to sleeping. One tablet or capsule of appropriate dosage is administered nightly (or prior to sleep) to the patient on a daily basis until the medical condition being treated is cured, or until the symptoms are sufficiently relieved. This drug treatment may be continued as needed to prevent, control or prevent disease symptoms.

It should be understood that some modification, alteration and substitution is anticipated and expected from those skilled in the art without departing from the teachings of the invention. Accordingly, it is appropriate that the following claims be construed broadly and in a manner consistent with the scope and spirit of the invention.

What is claimed is:

1. A time specific delayed release dosage formulation for administration once daily prior to sleep, which comprises:
   a biologically inert pellet;
   a drug layer coating the biologically inert pellet, said drug layer comprising a dosage form of a pharmaceutical agent and a binder agent, said binder agent and said pharmaceutical agent being present in a ratio of about 0.5:20; and
   an outer rate controlling layer coating the drug layer, said outer rate controlling layer comprising a water insoluble polymer, said water insoluble polymer being present in a total amount in the range of from about 5–12% of the total weight of the dosage formulation;
   wherein release of the pharmaceutical agent from the dosage formulation in vitro substantially corresponds to the following dissolution profile, as measured in water in a paddle apparatus according to U.S. Pharmacopeia XXII at 100 rpm:
   a) not more than about 8% of the pharmaceutical agent is released at about 5 hours from the time of the administration of the dosage formulation; and
   b) about 90% of the pharmaceutical agent is released at about 15 hours from the time of the administration of the dosage formulation.

2. The dosage formulation of claim 1 wherein said biologically inert pellet is a non-pareil pellet.

3. The dosage formulation of claim 2 wherein said non-pareil pellet comprises sugar.

4. The dosage formulation of claim 1 wherein said biologically inert pellet has a particle size of from about 25 to about 30 mesh.

5. The dosage formulation of claim 1 further comprising a drug sealing layer between the drug layer and the outer rate controlling layer.

6. The dosage formulation of claim 1 wherein said outer rate controlling layer additionally contains a lubricant.

7. The dosage formulation of claim 6, wherein said lubricant is magnesium stearate, calcium stearate, or zinc stearate.

8. The dosage formulation of claim 1 wherein said outer rate controlling layer comprises a poly(meth)acrylate polymer or a copolymer of acrylic and methacrylic acid esters, which is physiologically acceptable, water insoluble, and permeable to the release of said pharmaceutical agent.

9. The dosage formulation of claim 8 wherein the outer rate controlling layer comprises Eudragit NE 30D.

10. The dosage formulation of claim 8 wherein the outer rate controlling layer comprises from about 2 to about 10% magnesium stearate.

11. The dosage formulation of claim 1 wherein the outer rate controlling layer is coated with an enteric coating polymer.

12. The dosage formulation of claim 11 wherein concentration of said enteric polymer coat is about 4.5% to about 5% w/w of total weight of the dosage formulation.

13. The dosage formulation of claim 1 wherein the pharmaceutical agent comprises 40% to 50% w/w of total weight of the dosage formulation.

14. The dosage formulation of claim 1 in a tablet or capsule form.

15. The dosage formulation of claim 1 wherein the pharmaceutical agent is diltiazem.

16. The dosage formulation of claim 15 wherein following administration said dosage formulation provides from about 0 to less than about 20 ng of diltiazem released from the time of administration to about 5 hours after administration, followed by an increase of plasma concentration of diltiazem to a peak concentration of diltiazem at about 8 hours to about 12 hours after administration of the dosage formulation.

17. The dosage formulation of claim 16 wherein the peak concentration of diltiazem comprises about 90 ng/ml to about 110 ng/ml.

18. The dosage formulation of claim 1 wherein the binder agent is hydroxypropylmethyl cellulose.

19. The dosage formulation of claim 15 wherein the binder agent is hydroxypropylmethyl cellulose.

20. The dosage formulation of claim 19 wherein the water insoluble polymer is poly(meth)acrylate.

* * * * *